(12) United States Patent
Nakamura

(10) Patent No.: US 9,398,909 B2
(45) Date of Patent: Jul. 26, 2016

(54) NEEDLE HOLDER

(76) Inventor: Shu Nakamura, Inuyama (JP)

(*) Notice: Subject to any disclaimer, the term of this patent is extended or adjusted under 35 U.S.C. 154(b) by 1116 days.

(21) Appl. No.: 13/443,357

(22) Filed: Apr. 10, 2012

(65) Prior Publication Data

US 2012/0271329 A1    Oct. 25, 2012

(30) Foreign Application Priority Data

Apr. 25, 2011 (JP) ................. 2011-097329

(51) Int. Cl.
*A61B 17/062* (2006.01)
*A61B 17/29* (2006.01)

(52) U.S. Cl.
CPC ....... *A61B 17/062* (2013.01); *A61B 2017/2913* (2013.01); *A61B 2017/2924* (2013.01); *A61B 2017/2945* (2013.01)

(58) Field of Classification Search
CPC ..................... A61B 17/062; A61B 2017/2924; A61B 2017/2945; A61B 2017/2913
USPC .............. 606/146, 148, 149; 66/1 A, 93, 100, 66/108, 117, 120, 122
See application file for complete search history.

(56) References Cited

U.S. PATENT DOCUMENTS 5,833,697 A * 11/1998 Ludwick ................. 606/147
2011/0054499 A1 * 3/2011 Almodovar ............. 606/147

FOREIGN PATENT DOCUMENTS

JP    2007-054249 A    3/2007

* cited by examiner

*Primary Examiner* — Corrine McDermott
*Assistant Examiner* — Joshua Levine
(74) *Attorney, Agent, or Firm* — Westerman, Hattori, Daniels & Adrian, LLP

(57) ABSTRACT

A needle holder includes a first shaft on which a first gripping body is provided at a front end, and a second shaft on which a second gripping body is provided at a front end and which slides in an axial direction relative to the first shaft. The first gripping body and the second gripping body have continuous curved convex shapes at at least sides opposed to each other and abut against each other as the second shaft slides relative to the first shaft. An abutment keeping mechanism by which abutment between the first gripping body and the second gripping body is kept while the first shaft and the second shaft are separated from each other as the second shaft further slides relative to the first shaft in the same direction from a state where the first gripping body and the second gripping body abut against each other is provided.

7 Claims, 9 Drawing Sheets

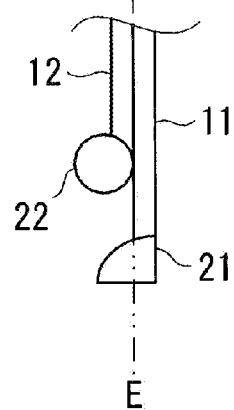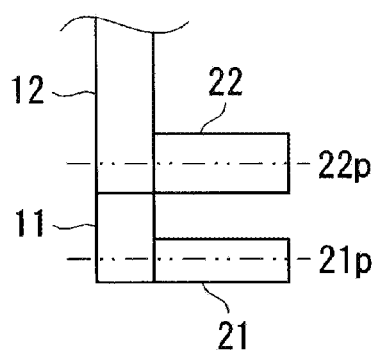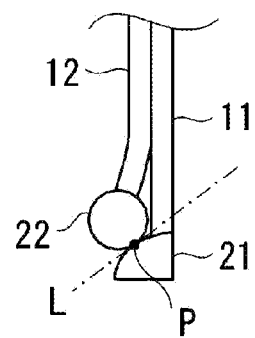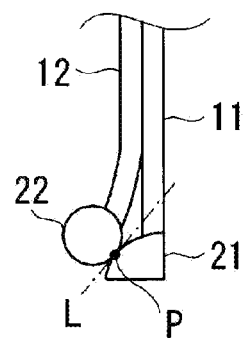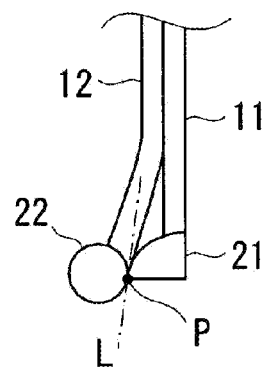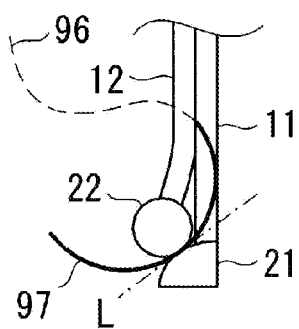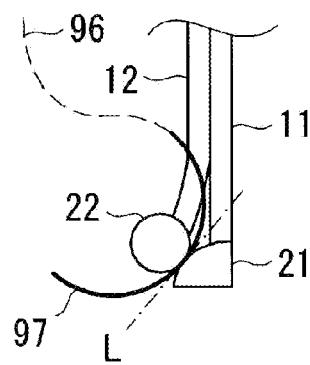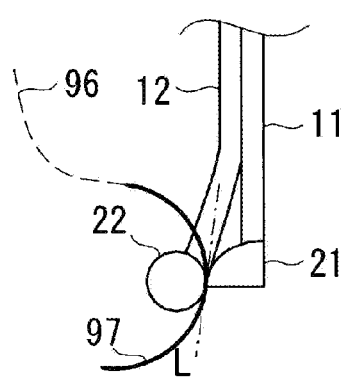

"Prior Art"

"Prior Art"

NEEDLE HOLDER

The present application is based on Japanese Priority Application No. 2011-097329 filed on Apr. 25, 2011 with the Japan Patent Office, the entire contents of which are hereby incorporated by reference.

BACKGROUND OF THE INVENTION

1. Field of the Invention

The present invention relates to a needle holder used for surgery in which tissue is sutured by using a circular arc-like needle, and in particular, relates to a needle holder suitable to endoscopic surgery.

2. Description of the Related Art

When tissue is sutured in surgery, a needle holder 100 as illustrated in FIG. 12A is used in general. The needle holder 100 has a configuration in which a pair of shafts 101 having gripping portions 102 provided at one ends and handle portions 103 provided at the other ends are pivotally fitted to each other in a rotationally movable manner about an axis 105 like scissors. The pair of gripping portions 102 are opened and closed with opening/closing operations of the handle portions 103. With this, a needle can be held between gripping surfaces 104 of the pair of gripping portions 102, which are opposed to each other. When a circular arc-like needle is gripped with such needle holder 100 to suture tissue, a direction of a needle 97 is changed by inclining axial directions (S) of the shafts with respect to a tissue 98 to be sutured as illustrated in FIG. 12C from a state where one end of the needle 97 is thrust into the tissue 98 as illustrated in FIG. 12B so that the needle 97 is made to penetrate through the tissue 98.

The endoscopic surgery is performed by inserting an instrument with an elongated thin handle and an endoscope into a cannula guided by a dilator or a trocar. For example, as illustrated in FIG. 14, a gripping forceps 110 for common endoscopic surgery has a pair of jaw portions 112 provided at a front end of an elongated shaft 111. The pair of jaw portions 112 can be opened and closed by operating a handle 113 provided at a base end side. Such an instrument for endoscopic surgery is used in a state of being inserted into an elongated cylindrical cannula 95. Therefore, motions of the instrument are inevitably limited. To be more specific, motions allowed for the instrument are substantially limited to a rotating motion (R direction in FIG. 14) about an axial core of the shaft 111 and a linear motion (forward/backward motions, Z direction in FIG. 14) along an axial direction of the shaft 111 except for motions unique to the instrument such as motions of the jaw portions 112 in the gripping forceps 110.

Therefore, when tissue is sutured endoscopically by gripping a needle with an instrument for endoscopic surgery, such as a gripping forceps, the axial direction of a shaft cannot be inclined unlike a usage method of the needle holder 100 as described above with reference to FIG. 12B and FIG. 12C. Accordingly, tissue cannot be sutured with a conventional instrument for endoscopic surgery. For example, in lumbar endoscope surgery, there are quite a few cases that dura mater injury is generated incidentally. Dura mater is injured in a splitting manner in a fiber direction. Therefore, as illustrated in FIG. 14, a dura mater injury 99 is generated in a direction (direction indicated by a line X in FIG. 14) intersecting with an axial direction of the cannula 95 (axial direction of the shaft 111).

In order to suture the injury generated in the above direction with a circular arc-like needle, the following operations need to be performed. That is, as illustrated in FIG. 13A, the needle 97 is inclined such that a front end thereof moves toward an inner portion of the tissue 98, and the end of the needle 97 is thrust into the tissue. Thereafter, as illustrated in FIG. 13B, the needle 97 is rotationally moved in a circumferential direction so that the front end of the needle 97 is made to exit to an outer side of a surface of the tissue 98. It is to be noted that in FIG. 13B, a state where the needle 97 is rotationally moved in the circumferential direction about a center point C of a circular arc. However, in actual suture surgery, when a needle is rotationally moved in a circumferential direction, the needle is not required to be rotationally moved about a center point of a circular arc accurately. In the specification, an expression "a circular arc-like needle is rotationally moved in a circumferential direction" is used including a case where a center point of an circular arc is slightly deviated between before and after the needle is rotationally moved.

However, in a conventional gripping forceps, even if the needle 97 is gripped such that the front end of the needle 97 moves toward the inner portion of the tissue 98 as illustrated in FIG. 13A, an axial direction (S1) of a shaft of the gripping forceps cannot be inclined in a state where the needle 97 is inserted into an elongated cannula. Therefore, in the conventional gripping forceps, the needle 97 cannot be rotationally moved in the circumferential direction in the above state. Accordingly, under the present circumstances, when an injury is generated in the direction that the injury cannot be sutured unless the needle 97 is rotationally moved in the circumferential direction as described above, the injury is sutured in the following manner. That is, in the above case, endoscopic surgery is stopped, a body surface is largely incised and the injury is sutured under direct vision or microscopically.

As a needle holder intended for inclining a circular arc-like needle, a needle holder in which a pair of needle holding pieces 121 are assembled in a scissors-like form as illustrated in FIGS. 15A to 15D has been proposed (see, Japanese Patent Application Laid-open No. 2007-54249). To be more specific, a gripping portion 122 having a perpendicular gripping surface 124 is attached to a front end of each needle holding piece 121 in a rotationally movable manner in the needle holder. The needle holder has a configuration in which each of a pair of gripping portions 122 rotates about an axial core 125 of itself so as to incline the needle 97. Therefore, the circular arc-like needle 97 cannot be rotated in the circumferential direction. It is to be noted that FIG. 15A and FIG. 15B illustrate a state before the pair of gripping portions 122 are rotated about the axial cores 125, and FIG. 15C and FIG. 15D illustrate a state after the pair of gripping portions 122 are rotated about the axial cores 125.

In addition, an instrument for endoscopic surgery needs to be reduced in size for being inserted into a cannula having a small diameter. However, the needle holder as disclosed in Japanese Patent Application Laid-open No. 2007-54249 is difficult to be reduced in size because the needle holder has a complicated configuration in which the pair of gripping portions 122 which are rotatable about the axial cores 125 are provided at front ends.

SUMMARY OF THE INVENTION

In view of the above circumstances, an object of the invention is to provide a needle holder which makes it possible to rotationally move a gripped circular arc-like needle in a circumferential direction without inclining an axial direction of a main body with a simple configuration.

In order to achieve the above object, according to an aspect of the invention, there is provided "a needle holder which grips a circular arc-like needle including a first shaft on which a first gripping body is provided at a front end, and a second shaft on which a second gripping body is provided at a front end and which slides in an axial direction relative to the first shaft. In the needle holder, the first gripping body and the second gripping body have continuous curved convex shapes at at least sides opposed to each other and abut against each other as the second shaft slides relative to the first shaft, and an abutment keeping mechanism by which abutment between the first gripping body and the second gripping body is kept while the first shaft and the second shaft are separated from each other as the second shaft further slides relative to the first shaft in the same direction from a state where the first gripping body and the second gripping body abut against each other is provided."

A mode in which the second shaft "slides in an axial direction relative to the first shaft" indicates a mode in which the second shaft slides relative to the first shaft which is not moved, a mode in which the first shaft slides relative to the second shaft which is not moved, or a mode in which both of the first shaft and the second shaft slide in opposite directions. It is to be noted that the "first shaft" and the "second shaft" are elongated bar-like members and cross-sectional shapes thereof are not particularly limited.

It is sufficient that the first gripping body and the second gripping body have continuous curved convex shapes at "at least sides opposed to each other". The first gripping body and the second gripping body can also have continuous curved convex shapes over the entire circumferences. The expression "continuous curved convex shape" indicates a shape of a convex form on the whole without a concave portion thereon. As a cross-sectional shape thereof, a circular shape, a circular-arc shape, an elliptical shape, an elliptical-arc shape, a spindle shape, and a hyperbolic shape can be exemplified.

In the needle holder having the above configuration, if the second shaft is made to slide relative to the first shaft in a direction of making closer to each other from a state where the first gripping body and the second gripping body are separated from each other in an axial direction of the needle holder, the first gripping body and the second gripping body abut against each other. If the second shaft is further made to slide relative to the first shaft from this state, the abutment state between the first gripping body and the second gripping body is kept while the first shaft and the second shaft are separated from each other with the abutment keeping mechanism.

The first gripping body and the second gripping body have continuous curved convex shapes at sides opposed to each other. Therefore, an abutment point moves along the continuous curved convex shapes as the second shaft slides relatively. Then, a gradient of a tangent line with respect to the abutment point gradually changes with the movement of the abutment point.

Accordingly, if the circular arc-like needle is held between the first gripping body and the second gripping body, the needle is held at the abutment point between the first gripping body and the second gripping body. The abutment point at which the needle is held moves as the second shaft slides relatively. Further, the gradient of the tangent line with respect to the abutment point gradually changes so that the circular arc-like needle is rotationally moved in the circumferential direction.

Accordingly, tissue can be sutured with the needle holder having the above configuration in the following manner. At first, the circular arc-like needle is held between the first gripping body and the second gripping body in a state where the first gripping body and the second gripping body abut against each other while the first shaft and the second shaft are separated from each other. In this state, if the first shaft and the second shaft are inserted into a cannula which is thrust into the body and extends in a direction intersecting with a tissue surface, the tangent line with respect to the abutment point (point at which the needle is held) between the first gripping body and the second gripping body is largely inclined with respect to the tissue surface. Therefore, a front end of the needle moves toward an inner portion of the tissue so that the front end of the needle can be thrust into the tissue. Then, if the first shaft and the second shaft are made closer to each other by making the second shaft slide relatively, an angle between the tangent line with respect to the abutment point between the first gripping body and the second gripping body and the tissue surface becomes gradually smaller. With this, the needle is rotationally moved in the circumferential direction, is made to penetrate through the tissue, and then, a needle tip can be made to exit to the outer side of the tissue. Thereafter, if the needle tip is held by another instrument and the second shaft is further made to slide relative to the first shaft, the first gripping body and the second gripping body are separated from each other in the axial directions of the first shaft and the second shaft, respectively. Therefore, the held needle is released.

As described above, with the needle holder according to the aspect of the invention, the circular arc-like needle can be rotationally moved in the circumferential direction without inclining the axial directions of the first shaft and the second shaft, thereby performing suture surgery which cannot be performed with endoscopic surgery with a conventional technique. In addition, rotational movement of the needle in the circumferential direction and the release of the needle can be performed with a series of operations in which the first shaft and the second shaft are made to relatively slide in the same direction. Therefore, the operation is made easier.

Further, the needle holder according to the aspect of the invention does not include a rotating member or the like. Therefore, a configuration thereof is simple. Accordingly, the needle holder can be reduced in size. From a viewpoint of this, the needle holder is suitable for endoscopic surgery, which is used by being inserted into a cannula having a small diameter.

In the needle holder according to the aspect of the invention, in the above configuration, it is preferable that "the abutment keeping mechanism be a mechanism in which at least one of the first shaft and the second shaft is formed with a material having elasticity so as to be deflected in a direction in which the first shaft and the second shaft are separated from each other while keeping abutment between the first gripping body and the second gripping body as the second shaft further slides relative to the first shaft in the same direction from a state where the first gripping body and the second gripping body abut against each other."

In this configuration, at least one of the first shaft and the second shaft is elastically deformed so that the abutment between the first gripping body and the second gripping body is kept while the first shaft and the second shaft are separated from each other as the second shaft slides relatively. To be more specific, if the second shaft is further made to slide relative to the first shaft from a state where the first gripping body and the second gripping body abut against each other, at least one of the first shaft and the second shaft is deflected in a direction of being separated from each other and the first gripping body and the second gripping body are made pressure contact with each other with the elasticity. With this, as the abutment point moves along the continuous curved convex shapes as described above, the gradient of the tangent line with respect to the abutment point gradually changes so that the circular arc-like needle can be rotationally moved in the circumferential direction.

In the needle holder according to the aspect of the invention, instead of the above configuration, it is preferable that "the abutment keeping mechanism be a mechanism in which a clearance is provided between the first shaft and the second shaft, the first shaft and the second shaft are biased by a biasing member in directions of making closer to each other, and the biasing member has a biasing force capable of keeping abutment between the first gripping body and the second gripping body while allowing the first shaft and the second shaft to be separated from each other as the second shaft further slides relative to the first shaft in the same direction from a state where the first gripping body and the second gripping body abut against each other."

As the "biasing member" which biases the first shaft and the second shaft in the directions of making closer to each other, a coil spring or a rubber can be used.

With this configuration, even if the first shaft and the second shaft are formed by members having high rigidity, an operation of rotationally moving the needle held between the first gripping body and the second gripping body in the circumferential direction can be performed in the same manner as described above.

To be more specific, if the second shaft is made to slide relative to the first shaft so that the first gripping body and the second gripping body having the continuous curved convex shapes on opposed surfaces abut against each other, a force in a direction of separating the first shaft and the second shaft from each other acts on both of the shafts. In the above configuration, since the clearance is provided between the first shaft and the second shaft, the first shaft and the second shaft can be separated from each other. On the other hand, both the shafts are biased by the biasing member in the directions of making closer to each other. Therefore, the first gripping body and the second gripping body are made pressure contact with each other. Accordingly, the abutment point moves in a state the abutment is kept as the second shaft slides relatively. With this, as the abutment point moves along the continuous curved convex shapes, the gradient of the tangent line with respect to the abutment point gradually changes so that the circular arc-like needle is rotationally moved in the circumferential direction in the same manner as described above.

In the needle holder according to the aspect of the invention, in addition to the above configuration, it is preferable that "one surface of the first gripping body or the second gripping body be smooth and fine irregularities be formed on the other surface".

As a mode in which the "fine irregularities" are formed on one surface of the first gripping body or the second gripping body, a mode in which a large number of fine dots are provided on the surface in a protruding manner, a mode in which a large number of extremely thin and shallow grooves are provided on the surface, and a mode in which the surface is made rough by chemically decaying the surface can be exemplified.

The needle holder according to the aspect of the invention is required to rotationally move the needle in the circumferential direction in a sliding manner with the movement of the abutment point between the first gripping body and the second gripping body while securely gripping the needle unlike a common gripping forceps which is required to hold a gripped target such that the target does not move. Therefore, one surface of the first gripping body or the second gripping body is made smooth such that the needle is easy to slide thereon and a slip-proof configuration with the fine irregularities is formed on the other surface thereof, thereby balancing an action of making the needle slide and an action of firmly gripping the needle.

As described above, a needle holder which makes it possible to rotationally move a gripped circular arc-like needle in a circumferential direction without inclining an axial direction of a main body with a simple configuration can be provided as an effect of the aspect of the invention.

BRIEF DESCRIPTION OF THE DRAWINGS

FIG. 2A is a partial front view illustrating a state where a first shaft and a second shaft are separated from each other in an axial direction on the needle holder of FIG. 1, and FIG. 2B is a partial side view illustrating the state of FIG. 2A.

FIG. 3A, FIG. 3B and FIG. 3C are partial front views for explaining motions of the needle holder of FIG. 1 at a front end side.

FIG. 4A, FIG. 4B and FIG. 4C are partial front views for explaining motions of a circular arc-like needle gripped by the needle holder of FIG. 1 in correspondence to FIG. 3A, FIG. 3B and FIG. 3C.

DESCRIPTION OF EXEMPLARY EMBODIMENTS

Hereinafter, a needle holder 1 as a first embodiment of the invention is described with reference to FIG. 1 to FIG. 4C.

Figure 1:
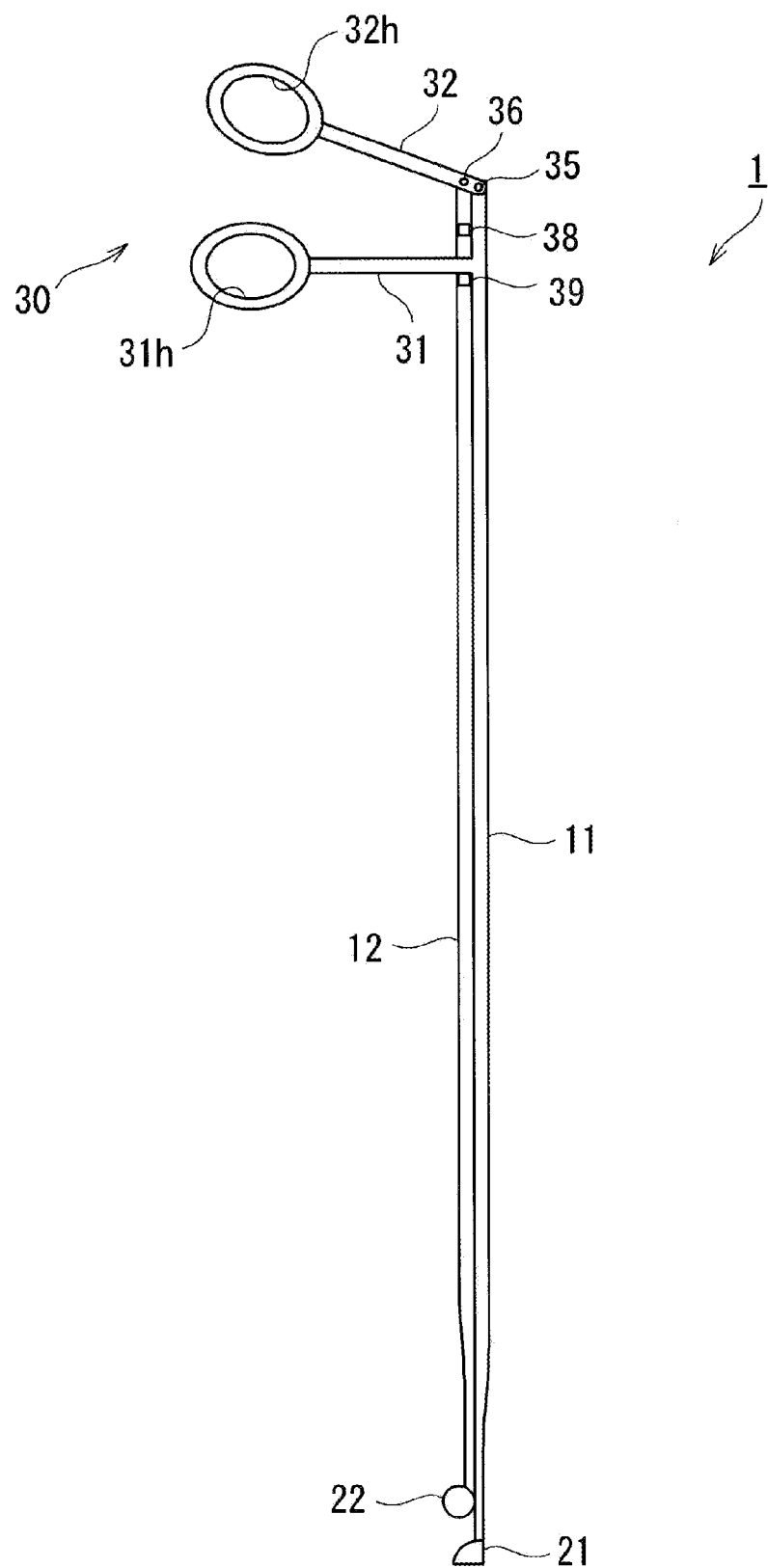
FIG. 1 is a front view illustrating a needle holder according to a first embodiment of the invention.

As illustrated in FIG. 1, the needle holder 1 includes a first shaft 11 and a second shaft 12. A first gripping body 21 is provided at a front end of the first shaft 11. A second gripping body 22 is provided at a front end of the second shaft 12 and the second shaft 12 slides relative to the first shaft 11 in an axial direction. The first gripping body 21 and the second gripping body 22 have continuous curved convex shapes at at least sides thereof opposed to each other and abut against each other as the second shaft 12 slides relative to the first shaft 11. Further, the needle holder 1 includes an abutment keeping mechanism in which abutment between the first gripping body 21 and the second gripping body 22 is kept while the second shaft 12 and the first shaft 11 are separated from each other as the second shaft 12 further slides relative to the first shaft 11 in the same direction from a state where the first gripping body 21 and the second gripping body 22 abut against each other.

In the first embodiment, the above abutment keeping mechanism is realized as follows. That is, at least one of the first shaft 11 and the second shaft 12 is formed with a material having elasticity so as to be deflected in a direction in which the first shaft 11 and the second shaft 12 are separated from each other while keeping abutment between the first gripping body 21 and the second gripping body 22 as the second shaft 12 further slides relative to the first shaft 11 from the state where the first gripping body 21 and the second gripping body 22 abut against each other.

Further, in the embodiment, the first shaft 11 and the second shaft 12 are formed by solid members which are arranged in parallel. In addition, front end sides of the first shaft 11 and the second shaft 12 are formed to be thinner than base end sides. Note that the "base end" of the first shaft 11 indicates an end at a side opposite to a side at which the first gripping body 21 is provided and the "base end" of the second shaft 12 indicates an end at a side opposite to a side at which the second gripping body 22 is provided.

To be more specific, the first shaft 11 and the second shaft 12 have square bar-like shapes and surfaces thereof which are opposed to each other are parallel with each other. Further, the opposed surfaces of the first shaft 11 and the second shaft 12 are made slide contact with each other at the base end side. The surface of the first shaft 11, which makes slide contact with the second shaft 12, is assumed to be a first slide contact surface, and the surface of the second shaft 12, which makes slide contact with the first shaft 11, is assumed to be a second slide contact surface. Under the assumption, configurations which guide a sliding motion of the second shaft 12 relative to the first shaft 11 can be provided on the first slide contact surface and the second slide contact surface.

To be more specific, a configuration in which a protrusion (not illustrated) is provided on one of the first slide contact surface or the second slide contact surface along the axial direction and a groove (not illustrated) is provided on the other thereof along the axial direction so that the protrusion is fitted into the groove in a slidable manner can be employed. With this configuration, the sliding of the second shaft 12 relative to the first shaft 11 is guided in a direction in which the protrusion and the groove extend. Therefore, the sliding motion is made stable. It is to be noted that the front end sides of the first shaft 11 and the second shaft 12 are deflected in the directions of being separated from each other. Accordingly, the configurations for guiding the sliding motion are not provided at the front end sides of the first shaft 11 and the second shaft 12.

Further, the first gripping body 21 extends from the front end of the first shaft 11 in a direction orthogonal to the first shaft 11 and the second gripping body 22 extends from the front end of the second shaft 12 in the same direction as the first gripping body 21, that is, in the direction orthogonal to the second shaft 12. Accordingly, an axial core 21p of the first gripping body 21 and an axial core 22p of the second gripping body 22 are parallel with each other (see, FIG. 2B).

In addition, in the embodiment, a transverse cross section of the first gripping body 21 (cross section of the first gripping body 21, which is orthogonal to the axial core 21p) is a shape of a slightly flattened quarter-circular shape. To be more specific, the first gripping body 21 has flat surfaces at the front end side of first shaft 11 and at a side opposite to a side at which the first gripping body 21 is opposed to the second gripping body 22. That is to say, the first gripping body 21 is formed such that a surface opposed to the second gripping body 22 has a continuous curved convex shape. In addition, the first gripping body 21 projects to the side of the second shaft 12 beyond a virtual flat surface (E) (hereinafter, referred to as "virtual slide contact surface (E)") obtained by extending the first slide contact surface and the second slide contact surface (see, FIG. 2A). It is to be noted that since the first slide contact surface and the second slide contact surface abut against each other, the surface obtained by extending any of them can be considered to be the virtual slide contact surface (E).

Figure 5A:
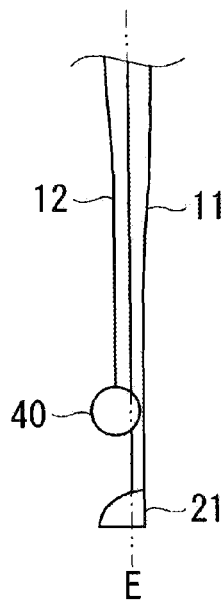
FIG. 5A to FIG. 5H are partial front views illustrating another modes of a first gripping body and a second gripping body.

On the other hand, a transverse cross section of the second gripping body 22 (cross section of the second gripping body 22, which is orthogonal to the axial core 22p) is a circular shape. That is, the second gripping body 22 has a continuous curved convex shape on the entire circumference. It is to be noted that in the embodiment, the second gripping body 22 has a shape that is not beyond the virtual slide contact surface (E). However, as illustrated in FIG. 5A, the second gripping body may be configured as a second gripping body 40 having a shape of projecting to the side of the first shaft 11 beyond the virtual flat surface (E).

The needle holder 1 includes an operation handle 30 for performing an operation of making the second shaft 12 slide relative to the first shaft 11. To be more specific, the operation handle 30 is constituted by a first handle 31 and a second handle 32. The first handle 31 is firmly attached at a position which is slightly closer to the front end side from the base end of the first shaft 11. The first handle 31 extends in a direction across the second shaft 12 and includes a first finger hole 31h through which a finger of a user (surgeon) is inserted. On the other hand, the second handle 32 is axially supported by an axis 35 at the base end of the first shaft 11 in a rotationally movable manner. With this, the second handle 32 is axially supported by an axis 36 at the base end of the second shaft 12 in a rotationally movable manner. Further, the second handle 32 extends in a direction of making an acute angle with respect to the first handle 31 and includes a second finger hole 32h through which a finger of a user is inserted.

With the above configuration, if the second handle 32 is operated to be made closer to the first handle 31, the second handle 32 is rotationally moved about the axis 35. Therefore, the second shaft 12 which axially supports the second handle 32 by the axis 36 is pressed toward the front end. With this operation, the second shaft 12 slides to the front end side along the axial direction relative to the first handle 31. It is to be noted that a protruding stopper 38 and a protruding stopper 39 are provided on the second shaft 12. The protruding stopper 38 abuts against the first handle 31 so as to limit a motion of the second shaft 12 when the second shaft 12 slides to the front end side. The protruding stopper 39 abuts against the first handle 31 so as to limit a motion of the second shaft 12 when the second shaft 12 slides to the base end side.

Further, in a state where the first handle 31 abuts against the stopper 39, that is, in a state where the second shaft 12 is located at the most base end side relative to the first shaft 11, the second gripping body 22 is separated from the first gripping body 21 to the base end side.

Next, an operation and a usage method of the needle holder 1 are described. At first, the second shaft 12 is made to slide to the front end side by operating the operation handle 30. With this, the second gripping body 22 gradually makes closer to and abuts against the first gripping body 21 (see, FIG. 3A) from a state in which the second gripping body 22 is separated from the first gripping body 21 (see, FIGS. 2A and 2B) because the first gripping body 21 projects to the side of the second gripping body 22 beyond the virtual slide contact surface (E).

If the second shaft 12 is further made to slide to the front end side from the above state, the second shaft 12 is elastically deformed so as to be deflected while the second gripping body 22 is made pressure contact with the first gripping body 21. With this, an abutment point (P) between the first gripping body 21 and the second gripping body 22 moves toward the front end and a gradient of a tangent line (L) with respect to the abutment point (P) changes (see, FIG. 3B). Then, in a state where the second shaft 12 slides to the front end side to a point at which further sliding of the second shaft 12 is limited with abutment between the stopper 38 and the first handle 31, a direction in which the tangent line (L) with respect to the abutment point (P) extends approximates to a direction parallel with the axial direction of the second shaft 12 (see, FIG. 3C).

Accordingly, when the first gripping body 21 and the second gripping body 22 are made into an abutment state as illustrated in FIG. 3A from the state of being separated from each other as illustrated in FIGS. 2A and 2B, if the circular arc-like needle 97 is made to be held between the first gripping body 21 and the second gripping body 22, the needle 97 is held in a state where a needle tip directs to the base end side of the needle holder 1 as illustrated in FIG. 4A. It is to be noted that the needle 97 is made to be held between the first gripping body 21 and the second gripping body 22 such that the circular arc thereof opens to the base end side. Further, a surgical suture 96 is adhered to one end of the needle 97.

If the second shaft 12 is made to slide to the front end side in the state where the needle 97 is held between the first gripping body 21 and the second gripping body 22, the abutment point (P) moves along the convex shape of the first gripping body 21. Then, when the abutment point (P) moves to a position as illustrated in FIG. 3B, the needle 97 is held in a state where the needle tip is inclined toward the front end side of the needle holder 1 as illustrated in FIG. 4B. Further, if the second shaft 12 is further made to slide to the front end side, the second shaft 12 is further deflected so as to be largely separated from the first shaft 11 and the abutment point (P) moves to a position as illustrated in FIG. 3C. At this time, as illustrated in FIG. 4C, the needle 97 is made into a state of being largely inclined. In this state, if the front end side of the needle holder 1 is inserted into a cannula which is thrust toward tissue to be sutured, the front end of the needle 97 moves toward an inner portion of the tissue. Accordingly, the front end of the needle 97 can be thrust into the tissue.

Then, if the second shaft 12 is made to slide to the base end side by operating the operation handle 30, the abutment point (P) between the first gripping body 21 and the second gripping body 22 moves to the base end side in an opposite direction to the above direction. With this operation, a gradient of the tangent line (L) with respect to the abutment point (P) changes so that the needle 97 rotationally moves in the circumferential direction. That is to say, a posture of the needle 97 changes from the state in FIG. 4C to the state in FIG. 4A through the state in FIG. 4B such that the front end gradually goes up. With this, the needle 97 penetrates through the tissue so that the front end of the needle 97 exits to the upper side with respect to a tissue surface. Therefore, the front end of the needle 97 is gripped by an instrument (gripping forceps or the like) which is different from the needle holder 1.

Then, if the second shaft 12 is further made to slide to the base end side, the second gripping body 22 is made into a state of being separated from the first gripping body 21 as illustrated in FIGS. 2A and 2B. Therefore, the needle 97 gripped by the needle holder 1 is released. Thereafter, the needle 97 and the surgical suture 96 are drawn out to the outside of the cannula by drawing out the different instrument which grips the front end of the needle 97 from the cannula.

The surgical suture penetrates through the tissue at one side of an injury with the above operations. Then, the surgical suture is made to penetrate through the tissue at the other side of the injury with the same operation. Thereafter, the needle 97 is drawn out from the cannula, a knot is formed with the surgical suture, and the knot is moved to a suture place with a knot pusher. With this, the injury is completed to be fixed with the surgical suture.

As described above, with the needle holder 1 according to the embodiment, the needle 97 can be held and released by the first gripping body 21 and the second gripping body 22 with the operation of making the second shaft 12 slide relative to the first shaft 11. In addition, the circular arc-like needle 97 held between the first gripping body 21 and the second gripping body 22 can be rotationally moved in the circumferential direction. This makes it possible to suture an injury at a site, which cannot be sutured in endoscopic surgery with a conventional technique.

At this time, the rotational movement of the needle 97 in the circumferential direction and the release of the needle 97 can be performed as a series of motions of making the second shaft 12 slide relative to the first shaft 11 in one direction after holding the needle 97 between the first gripping body 21 and the second gripping body 22. Therefore, the needle holder 1 according to the embodiment is operated easily.

Further, the first gripping body 21 and the second gripping body 22 extend in the directions orthogonal to the axial directions of the first shaft 11 and the second shaft 12, respectively. Therefore, when the needle 97 is rotationally moved in the circumferential direction, the first shaft 11 and the second shaft 12 and the needle 97 are not interfered with each other.

In addition, in the embodiment, since the first shaft 11 and the second shaft 12 are arranged in parallel and slide, they can have substantially the same diameters. With this, the first shaft 11 and the second shaft 12 can be ensured to have thicknesses at a certain degree. Moreover, both of the first shaft 11 and the second shaft 12 are formed by solid members. Accordingly, strengths of the first shaft 11 and the second shaft 12 can be enhanced.

Furthermore, the first shaft 11 and the second shaft 12 are formed such that the front end sides thereof are made thinner than the base end sides thereof. In other words, portions to be deflected in the direction in which the first shaft 11 and the second shaft 12 are separated from each other with the abutment between the first gripping body 21 and the second gripping body 22 are formed to be thinner and portions at the base end side, which are not to be deflected, are formed to be thick. With this configuration, even when the entire shafts are formed with the same material, the base end sides thereof can be formed to have high rigidity and the front end sides can be made easy to be deflected.

Further, the needle holder 1 has an extremely simple configuration. Therefore, the needle holder 1 can be easily reduced in size and can be inserted into a cannula having a small diameter.

Figure 5B:
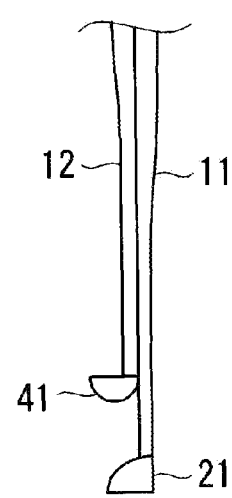

In addition, in the embodiment, the transverse cross section of the second gripping body 22 is a circular shape. This makes it possible to smoothly guide the rotational movement of the circular arc-like needle 97 in the circumferential direction. It is to be noted that even with a second gripping body 41 having a transverse cross section of a semicircular shape, which has a flat surface at the base end side thereof, as illustrated in FIG. 5B, the above guiding action can be also obtained in the same manner as the second gripping body 22.

On the other hand, the transverse cross section of the first gripping body 21 is a shape like a quarter-circular shape and the front end side thereof is a flat surface. Therefore, the needle 97 gripped by the needle holder 1 can be sufficiently made closer to tissue to be sutured. Further, a surface of the first gripping body 21 at the side opposite to the side at which the first gripping body 21 is opposed to the second gripping body 22 is a flat surface. Therefore, in endoscopic surgery in which operations need to be performed in a narrow space, there is an advantage that an operable space is easy to be ensured in the cannula.

Figure 5C:
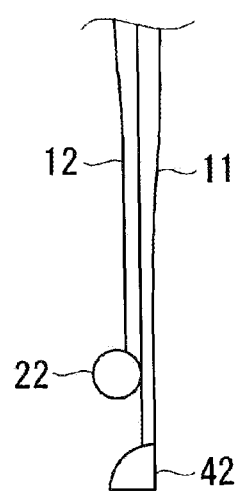
Figure 5D:
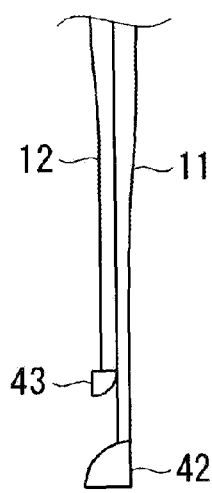

It is to be noted that the first gripping body can be configured as a first gripping body 42 having a transverse cross section of an accurate quarter-circular shape as illustrated in FIG. 5C. Further, the first gripping body and the second gripping body can be configured to have transverse cross sections as illustrated in FIG. 5D to FIG. 5H in addition to the shapes as described above. FIG. 5D illustrates an example in which the first gripping body 42 having the transverse cross section of the quarter-circular shape as illustrated in FIG. 5C and a second gripping body 43 having a transverse cross section of the same quarter-circular shape are combined. In the example as illustrated in FIG. 5D, surfaces of second gripping body 43 at the base end side and at a side opposite to the side at which the second gripping body 43 is opposed to the first gripping body 42 are flat surfaces.

Figure 5E:
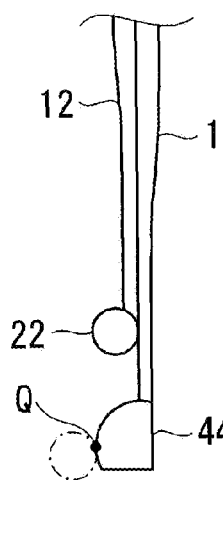
Figure 5F:
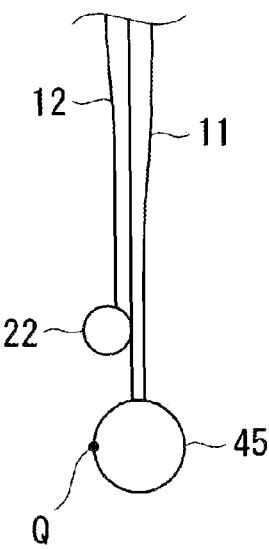
Figure 5G:
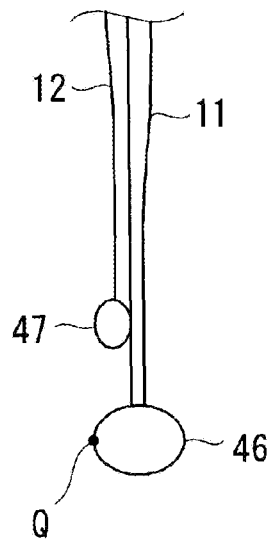
Figure 5H:
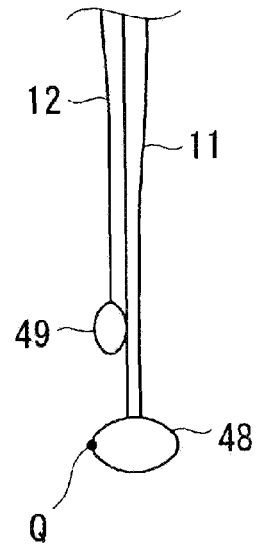

Further, FIG. 5E illustrates an example in which a first gripping body 44 of which outer circumferential shape of a transverse cross section is an approximately one-third-circular arc shape at the side of the second gripping body and the second gripping body 22 having the transverse cross section of the circular shape are combined. FIG. 5F illustrates an example in which a first gripping body 45 and the second gripping body 22 having transverse cross sections of circular shapes are combined. FIG. 5G illustrates an example in which a first gripping body 46 and a second gripping body 47 having transverse cross sections of elliptical shapes are combined. FIG. 5H illustrates an example in which a first gripping body 48 and a second gripping body 49 having transverse cross sections of hyperbolic shapes are combined.

Each of the first gripping bodies 44, 45, 46, 48 as illustrated in FIG. 5E to FIG. 5H has such a shape that a surface opposed to the second gripping body gradually expands from the base end side of the needle holder toward the second gripping body, and is curved so as to be farther from the second gripping body toward the front end side of the needle holder beyond a most expanded point (Q). When the first gripping body has such shape, in a state where the second gripping body moves while abutting against the first gripping body so as to be located at the front end side beyond the point (Q) (indicated by a dashed-dotted line in FIG. 5E), there is an advantage that the needle is stably held between the first gripping body and the second gripping body. That is to say, a force in the direction in which the second shaft is made closer to the first shaft acts on the second shaft all the time with an abutment keeping mechanism of making the second gripping body pressure contact with the first gripping body. Therefore, when the abutment point is located at the base end side with respect to the point (Q), the abutment point is easy to move to the base end side unless the operation handle is kept to be gripped so as to hold a position of the second shaft relative to the first shaft. In contrast, when the abutment point is located at the front end side beyond the point (Q), an expanded portion in the vicinity of the point (Q) serves as a barrier so that the abutment point is difficult to move to the base end side. Therefore, even if the operation handle is not kept to be gripped, the needle can be stably held with the abutment between the first gripping body and the second gripping body.

In addition, when the abutment point is located at the front end side beyond the point (Q), a needle tip of the held needle is largely inclined toward an inner portion of tissue. Therefore, in this case, there is also an advantage that the needle is easy to be thrust into the tissue.

Figure 6:
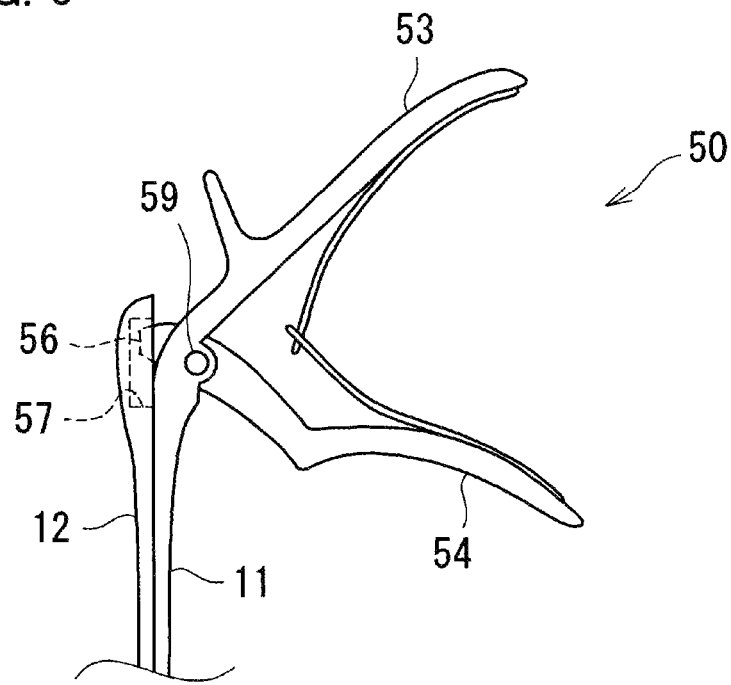
FIG. 6 is a partial front view illustrating another mode of an operation handle of the needle holder according to the first embodiment.

Moreover, as an operation handle, the operation handle 30 having a configuration in which the first handle 31 is firmly fixed to the first shaft 11, and the second handle 32 is axially supported on the end of the first shaft 11 in a rotationally movable manner and is also axially supported on the end of the second shaft 12 in a rotationally movable manner has been described above. However, the operation handle is not limited thereto. For example, an operation handle 50 as illustrated in FIG. 6 can be employed as the operation handle of the needle holder 1. Note that the operation handle 50 has a configuration which is similar to the configuration of the above operation handle 30 in points that a first handle 53 is integrated with the first shaft 11 and a second handle 54 is axially supported on the end of the first shaft 11 with an axis 59 in a rotationally movable manner. The operation handle 50 is mainly different from the operation handle 30 in the following points. That is, on the operation handle 50, a protrusion 56 on a front end of the second handle 54 moves in a groove 57 provided on an opposed surface of the second shaft 12 with the rotational movement of the second handle 54 to press an inner wall of the groove 57 so that the second shaft 12 slides to the front end side or the base end side.

Next, a needle holder according to a second embodiment is described. The needle holder in second embodiment is different from the needle holder 1 in the first embodiment in a configuration in which the first shaft and the second shaft slide. That is to say, in the needle holder 1, the first shaft 11 and the second shaft 12 are arranged in parallel and make slide contact with each other at the base end sides as the second shaft 12 slides. On the other hand, in the second embodiment, one of the first shaft or the second shaft is formed into a partially cylindrical shape. The other shaft is inserted through the cylindrical portion and moves in the cylindrical portion along the axial direction. A case in which the first shaft has the cylindrical portion is described as an example here.

Figure 7:
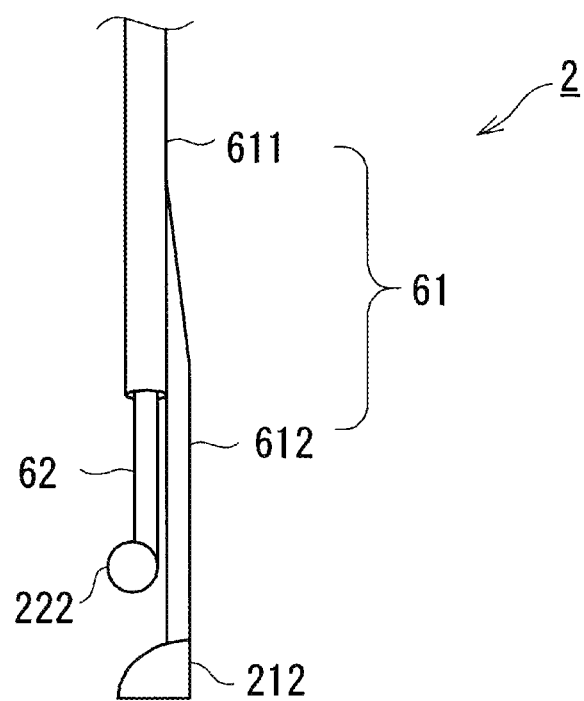
FIG. 7 is a partial front view illustrating a needle holder according to a second embodiment of the invention.

As is described in detail, as illustrated in FIG. 7, a first shaft 61 of a needle holder 2 according to the second embodiment is constituted by a cylindrical portion 611 at a base end side and an elongated bar-like rod portion 612 which is firmly fixed to an outer circumferential surface of the cylindrical portion 611. A second shaft 62 is inserted through the cylindrical portion 611. A first gripping body 212 is provided at a front end of the rod portion 612 and a second gripping body 222 is provided at a front end of the second shaft 62. The first gripping body 212 and the second gripping body 222 have configurations which are similar to those of the first gripping body 21 and the second gripping body 22 in the first embodiment or configurations as illustrated in FIG. 5A to FIG. 5H so that detail description thereof is not repeated.

Figure 8:
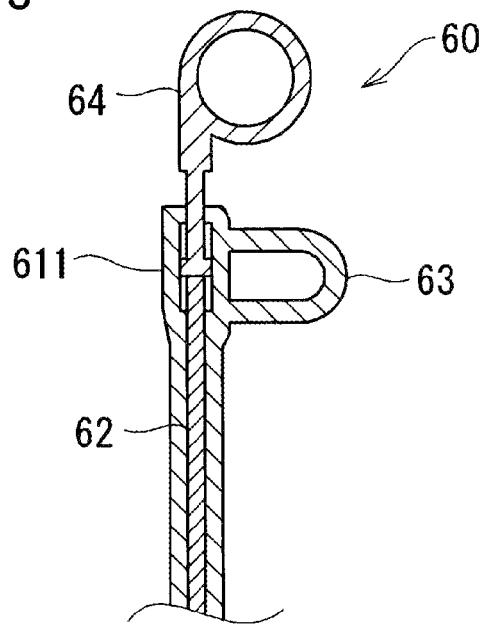
FIG. 8 is a longitudinal cross-sectional view illustrating an operation handle of the needle holder according to the second embodiment of the invention.

As an operation handle for performing an operation of making the second shaft 62 slide relative to the first shaft 61, an operation handle 60 as illustrated in FIG. 8 can be employed, for example. The operation handle 60 includes a first handle 63 which is firmly fixed to the cylindrical portion 611 and a second handle 64 which is firmly fixed to the base end side of the second shaft 62. If the second handle 64 is pulled so as to be separated from the first handle 63, the second shaft 62 slides to the base end side. On the contrary, if the second handle 64 is operated so as to be pressed toward the first handle 63, the second shaft 62 slides to the front end side. It is to be noted that the first handle and the second handle may have a configuration in which fingers are inserted through finger holes to operate them as illustrated in FIG. 8, or a configuration in which the handles are gripped with a palm of a hand like the above operation handle 50.

With the needle holder 2 according to the second embodiment, if the operation handle 60 is operated so as to make the second shaft 62 slide relative to the first shaft 61, a circular arc-like needle held between the first gripping body 212 and the second gripping body 222 can be rotationally moved in the circumferential direction and the needle can be released with a series of operations of making the second shaft 62 slide in the same direction in the same manner as the needle holder 1 according to the first embodiment.

Figure 9:
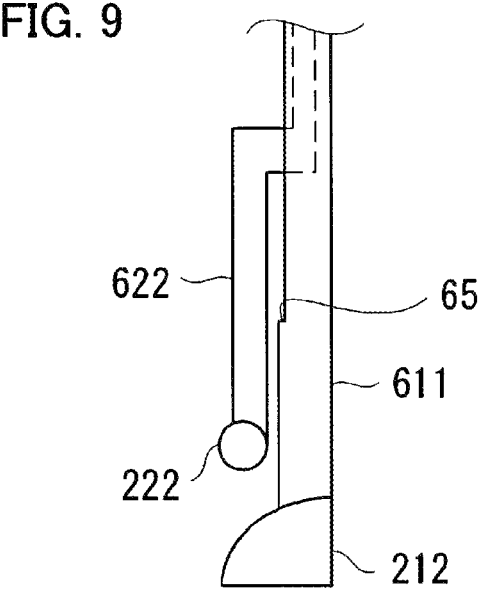
FIG. 9 is a partial front view illustrating a needle holder according to a variation of the second embodiment.

It is to be noted that as a variation of the second embodiment, as illustrated in FIG. 9, a configuration in which the first shaft is constituted by the cylindrical portion 611 only and the first gripping body 212 is provided at the front end side of the cylindrical portion 611 can be exemplified. An elongated slit 65 along the axial direction is formed at the front end side of a side circumferential surface of the cylindrical portion 611. On the other hand, a second shaft 622 is bent at the front end side in a crank form. With this configuration, a base end side of the second shaft 622 can be inserted through the cylindrical portion 611 and the front end side of the second shaft 622 can be located at the outside of the cylindrical portion 611 through the slit 65. With this, the second gripping body 222 provided at the front end of the second shaft 622 slides along the axial direction of the cylindrical portion 611 at the outside of the cylindrical portion 611.

With the configuration in which the first gripping body 212 is directly provided on the cylindrical portion 611, the first gripping body 212 can be supported with a thicker member (having a large diameter) in comparison with a case where the first gripping body 212 is provided on the rod portion 612 which is firmly fixed to the outer circumferential surface of the cylindrical portion 611. The first shaft and the second shaft can perform the above operations even if both of them are formed with a material which is easy to be elastically deformed. However, the needle is held and rotationally moved in the circumferential direction more stably if one of the first shaft and the second shaft has high rigidity and the other one thereof is easy to be elastically deformed. In the variation, the first shaft and the second shaft can be configured by combining the cylindrical portion 611 having high rigidity and the second shaft 622 which has a smaller diameter than the cylindrical portion 611 for being inserted through the cylindrical portion 611 and is easy to be elastically deformed, thereby performing operations of holding the needle and rotationally moving the needle in the circumferential direction more stably.

Next, a needle holder according to a third embodiment is described. The needle holder in third embodiment is different from the needle holders in the first embodiment and the second embodiment in a point that one of a first shaft or a second shaft includes a cyclic portion on an end thereof. Further, in the third embodiment, an end of the other shaft projects to the shaft having the cyclic portion and the projecting portion constitutes a gripping body. A case in which the second shaft includes the cyclic portion is described as an example here.

Figure 10:
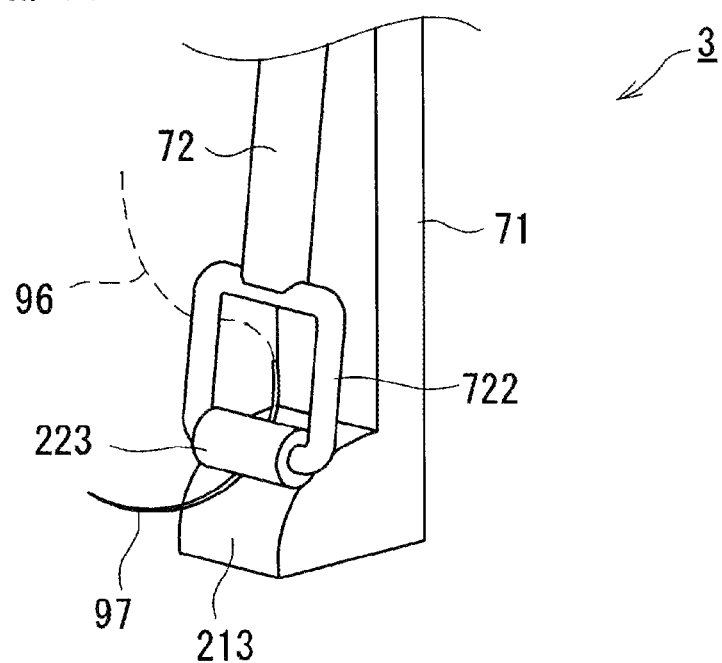
FIG. 10 is a partial perspective view illustrating a needle holder according to a third embodiment of the invention.

As is described in detail, as illustrated in FIG. 10, on a needle holder 3 according to the third embodiment, an end of a first shaft 71 expands out to a second shaft side in a continuous curved convex form and the expanding portion constitutes a first gripping body 213. On the other hand, a second shaft 72 includes a cyclic portion 722 on an end thereof. A part of the cyclic portion 722, which also corresponds to a front end of the second shaft 72, constitutes a second gripping body 223. FIG. 10 illustrates a case where the second gripping body 223 is formed in a columnar form. The second gripping body 223 has a continuous curved convex shape on the entire circumference.

With the needle holder 3 having the above configuration, if the second shaft 72 is made to slide relative to the first shaft 71, the circular arc-like needle 97 held between the first gripping body 213 and the second gripping body 223 can be rotationally moved in the circumferential direction and the needle can be released with a series of operations in the same manner as the needle holders 1, 2 according to the first embodiment and the second embodiment.

In addition, the needle holder 3 includes the cyclic portion 722. Therefore, when the needle 97 is rotationally moved in the circumferential direction, a posture of the needle 97 can be changed while locating a part of the needle 97 in an opening of the cyclic portion 722. Accordingly, on the needle holder 3, when the needle 97 is rotationally moved in the circumferential direction, both of the first shaft 71 and the second shaft 72 are not interfered with the needle 97. Further, on the needle holder 3, a space occupied by the first gripping body and the second gripping body is smaller in comparison with the needle holders 1, 2 in which the first gripping body and the second gripping body project in the directions orthogonal to the axial directions of the first shaft and the second shaft, respectively. Therefore, there is an advantage that a larger operable space can be ensured in the cannula having a small diameter.

Next, a needle holder according to a fourth embodiment is described. The needle holder in the fourth embodiment is different from the needle holders 1, 2, 3 in the first embodiment to the third embodiment in an abutment keeping mechanism. That is to say, an abutment keeping mechanism in the fourth embodiment is realized by a clearance provided between a first shaft and a second shaft and a biasing member which biases the first shaft and the second shaft in directions of making closer to each other.

Figure 11:
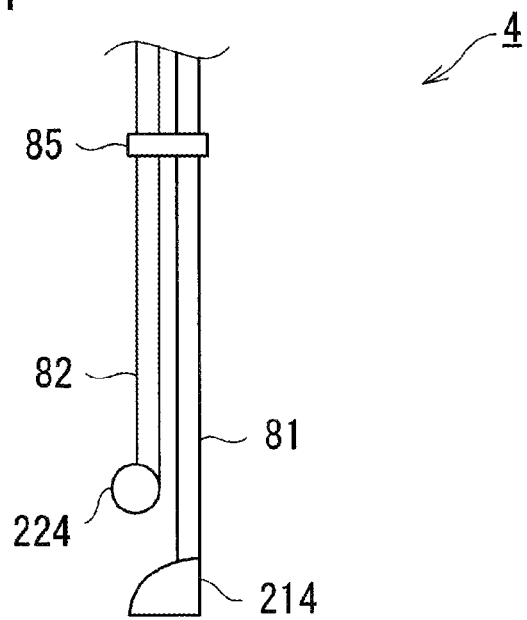
FIG. 11 is a partial front view illustrating a needle holder according to a fourth embodiment of the invention.
Figure 12A:
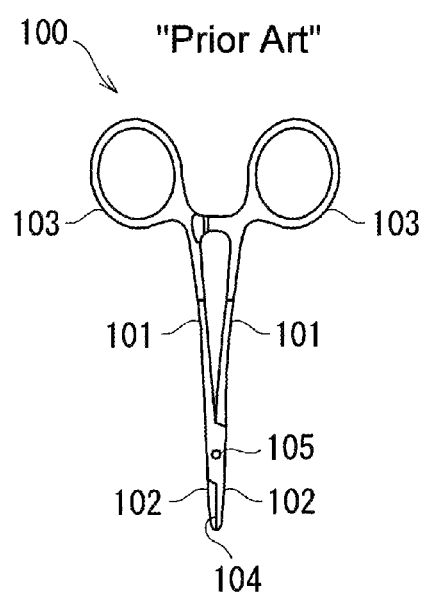
FIG. 12A is a front view illustrating a conventional needle holder.
Figure 12B:
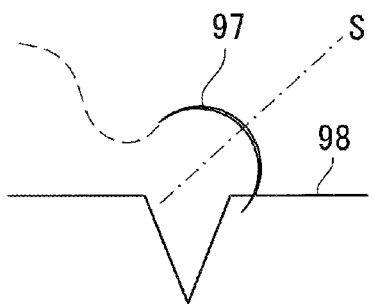
FIG. 12B and FIG. 12C are views for explaining a method of using the needle holder of FIG. 12A.
Figure 12C:
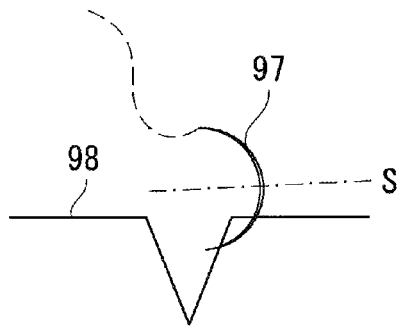
Figure 13A:
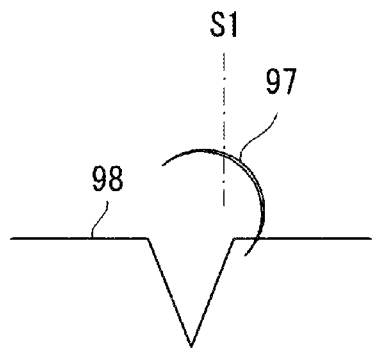
FIG. 13A and FIG. 13B are views for explaining motions of a needle required for the needle holder according to the invention.
Figure 13B:
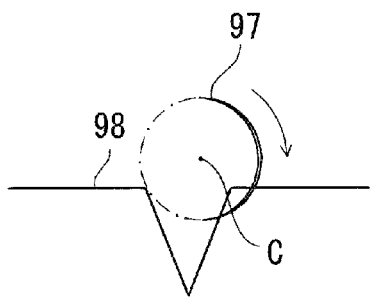
Figure 14:
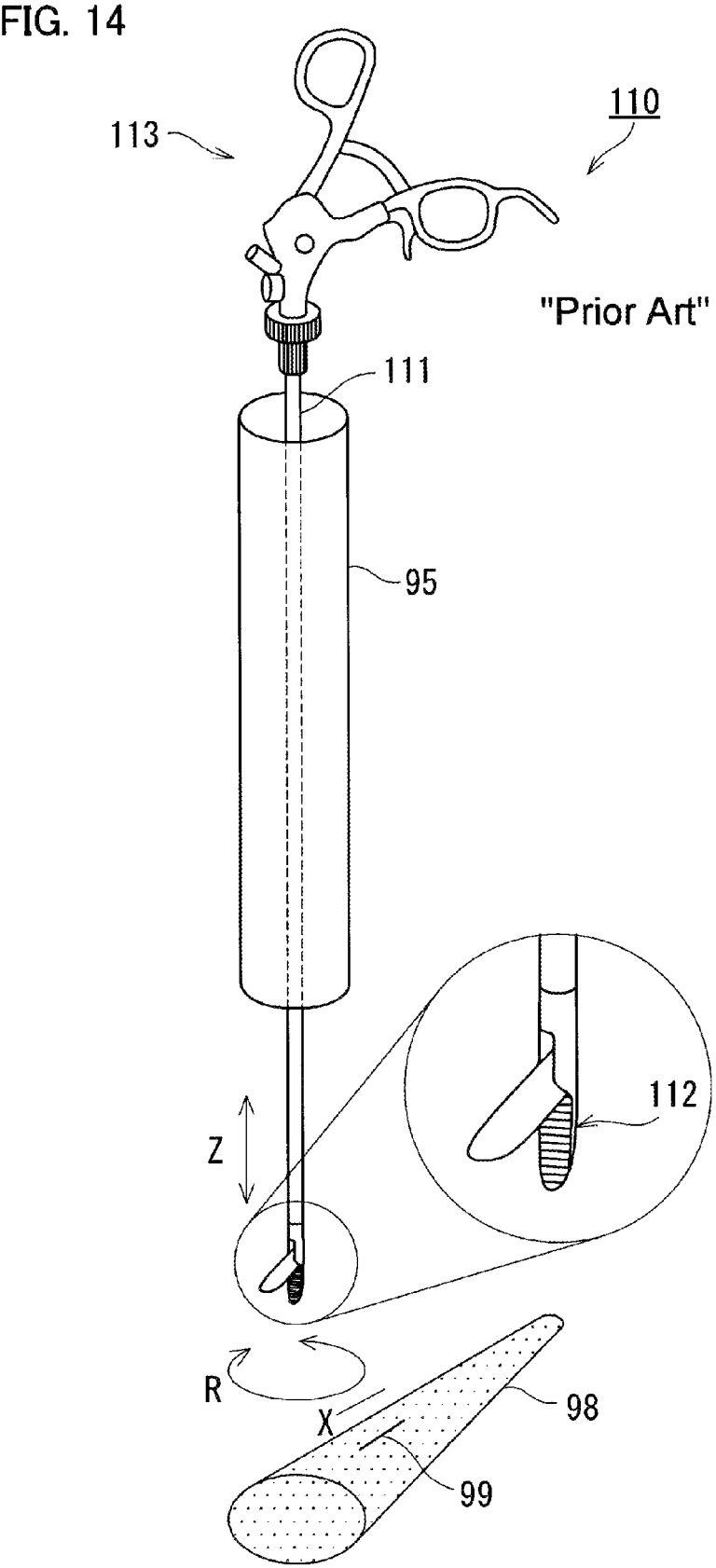
FIG. 14 is a descriptive view illustrating a conventional instrument for endoscopic surgery.
Figure 15A:
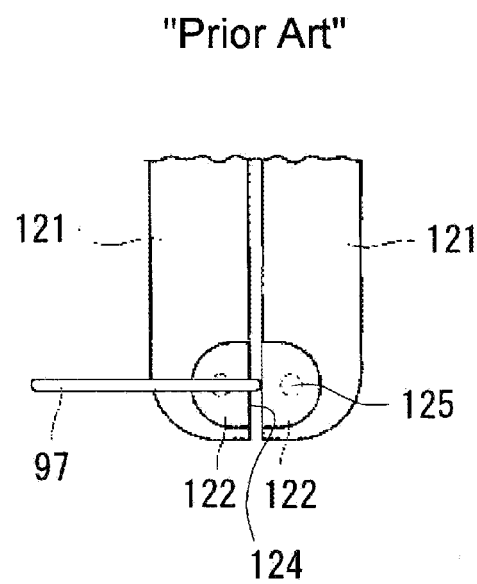
FIG. 15A to FIG. 15D are views for explaining gripping of a needle on a needle holder as disclosed in Japanese Patent Application Laid-open No. 2007-54249.
Figure 15B:
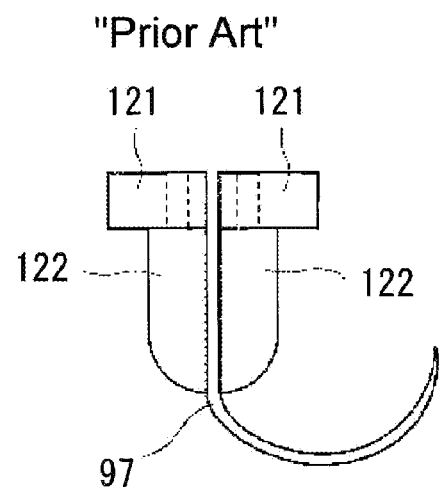
Figure 15C:
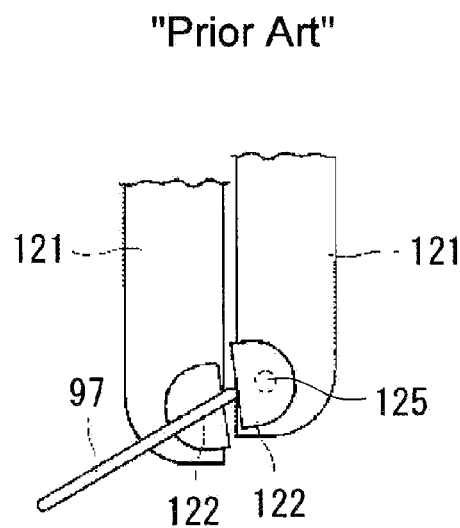
Figure 15D:
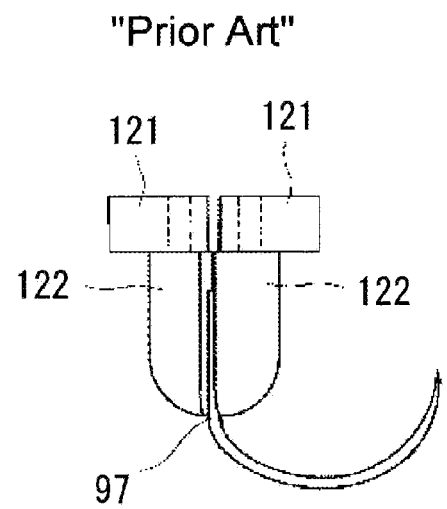

As is described in detail, as illustrated in FIG. 11, a needle holder 4 according to the fourth embodiment includes a first shaft 81 on which a first gripping body 214 is provided at a front end and a second shaft 82 on which a second gripping body 224 is provided at a front end and which slides in an axial direction relative to the first shaft 81. In the needle holder 4, the first gripping body 214 and the second gripping body 224 have continuous curved convex shapes at at least sides opposed to each other and abut against each other as the second shaft 82 slides relative to the first shaft 81. Further, the clearance is provided between the first shaft 81 and the second shaft 82. In addition, the first shaft 81 and the second shaft 82 are biased by a biasing member 85 in the directions of making closer to each other. The biasing member 85 has a biasing force capable of keeping abutment between the first gripping body 214 and the second gripping body 224 while allowing the first shaft 81 and the second shaft 82 to be separated from each other as the second shaft 82 further slides relative to the first shaft 81 in the same direction from a state where the first gripping body 214 and the second gripping body 224 abut against each other.

It is to be noted that the first gripping body and the second gripping body in the fourth embodiment can have configurations that are the same as those in the first embodiment, configurations as illustrated in FIG. 5A to FIG. 5H, or configurations that are the same as those in the third embodiment so that detail description is not repeated.

The needle holder 4 is operated in the following manner. If the second shaft 82 is made to slide relative to the first shaft 81 so that the first gripping body 214 and the second gripping body 224 abut against each other, a force in a direction of separating the first shaft 81 and the second shaft 82 from each other acts on the first shaft 81 and the second shaft 82. Since the clearance is provided between the first shaft 81 and the second shaft 82, both of the first shaft 81 and the second shaft 82 can be separated from each other. On the other hand, both the shafts are biased by the biasing member 85 in the directions of making closer to each other. With this, the first gripping body 214 and the second gripping body 224 are made pressure contact with each other and an abutment point moves in a state where abutment between the first gripping body 214 and the second gripping body 224 is kept as the second shaft 82 slides.

Accordingly, if the circular arc-like needle is held at the abutment point between the first gripping body 214 and the second gripping body 224, the needle can be rotationally moved in the circumferential direction and the needle can be released with a series of operations with the movement of the abutment point as the second shaft 82 slides in the same manner as the needle holders 1, 2, 3 according to the first embodiment to the third embodiment. Further, on the needle holder 4 according to the fourth embodiment, both of the first shaft 81 and the second shaft 82 can be formed with a material having high rigidity so that the entire strength of the needle holder 4 can be enhanced.

It is to be noted that in any of the needle holders 1, 2, 3, 4 according to the first embodiment to the fourth embodiment, one surface of the first gripping body or the second gripping body can be formed to be smooth and fine irregularities can be formed on the other surface thereof. For example, a surface of the second gripping body, which makes inner contact with the circular arc-like needle, can be formed to be smooth and fine irregularities can be formed on a surface of the first gripping body, which makes outer contact with the circular arc-like needle.

With this configuration, the needle is held between the smooth surface and the surface having the fine irregularities. This makes it possible to make the needle which is rotationally moved in the circumferential direction easy to slide with abutment against the smooth surface and firmly grip the needle of which posture is changed while rotationally moving in the circumferential direction with a slip-proof action with the fine irregularities.

As described above, the invention has been described by taking preferred embodiments as examples. However, the invention is not limited to the embodiments. Various improvements and changes in design can be made in a range without departing from a scope of the invention as will be described later.

For example, in the first embodiment and the second embodiment, a case where the first gripping body and the second gripping body extend in the directions orthogonal to the first shaft and the second shaft, respectively, has been described. However, the invention is not limited thereto and a configuration in which the first gripping body and the second gripping body extend in the directions intersecting with the axial directions of the first shaft and the second shaft, respectively, for example, directions of making obtuse angles with respect to the first shaft and the second shaft, respectively, can be employed.

Further, in the first embodiment to the fourth embodiment, a case where the second shaft slides relative to the first shaft has been described. However, the invention is not limited thereto and it is sufficient that the first shaft and the second shaft slide relatively.

In addition, the first shaft and the second shaft are not limited to have straight bar-like shapes, and may extend in the axial directions while twisting with each other and slide in the axial directions relatively.

What is claimed is:

1. A needle holder which grips a circular arc-like needle, comprising:
   a first elongated shaft extending from a base end forward to a front end and having a first gripping body at said front end, and
   a second elongated shaft extending from a base end forward to a front end and having a second gripping body at said front end, said second elongated shaft being mounted in a manner to slide in an axial direction relative to the first shaft, wherein
   the first gripping body has a first continuous curved convex shape facing rearward from the front end and the second gripping body has a second continuous curved convex shape facing said first continuous curved convex shape in a manner to oppose each other and abut against each other at an abutment point as the second shaft slides relative to the first shaft forward in said axial direction to an abutment state, and
   an abutment keeping mechanism that is configured to maintain abutment between the first gripping body and the second gripping body with said abutment point sliding in said axial direction by moving around a curvature of said first continuous curved convex shape and with the first shaft and the second shaft separating from each other at their front ends as the second shaft slides further forward in said axial direction relative to the first shaft from said abutment state.

2. The needle holder according to claim 1, wherein
   the abutment keeping mechanism is a mechanism in which at least one of the first shaft and the second shaft is formed with a material having elasticity so as to be deflected in a direction in which the first shaft and the second shaft are separated from each other while keeping abutment between the first gripping body and the second gripping body as the second shaft slides further forward in said axial direction relative to the first shaft from said abutment state.

3. The needle holder according to claim 1, wherein
   the abutment keeping mechanism is a mechanism in which a clearance is provided between the first shaft and the second shaft, the first shaft and the second shaft are biased by a biasing member in directions of making closer to each other, and the biasing member has a biasing force capable of keeping abutment between the first gripping body and the second gripping body while allowing the first shaft and the second shaft to be separated from each other as the second shaft slides further forward in said axial direction relative to the first shaft from said abutment state.

4. The needle holder according to any one of claim 2 or 3, wherein
   one surface of the first gripping body or the second gripping body is smooth and fine irregularities are formed on the other surface.

5. The needle holder according to claim 1, wherein said first continuous curved convex shape curves around an axial core of said first gripping body that extends transverse to said axial direction and said second continuous curved convex shape curves around an axial core of said second gripping body that extends transverse to said axial direction.

6. The needle holder according to claim 5, wherein the axial core of the first gripping body is parallel to the axial core of the second gripping body.

7. The needle holder according to claim 5, wherein said axial direction is orthogonal to both the axial core of the first gripping body and the axial core of the second gripping body.

* * * * *